(12) United States Patent
Termanini

(10) Patent No.: US 8,313,531 B2
(45) Date of Patent: Nov. 20, 2012

(54) INTERLOCKING REVERSE HIP PROSTHESIS AND METHOD

(75) Inventor: Zafer Termanini, Cedar Grove, NJ (US)

(73) Assignee: Hip Innovation Technology LLC, West Orange, NJ (US)

( * ) Notice: Subject to any disclaimer, the term of this patent is extended or adjusted under 35 U.S.C. 154(b) by 145 days.

(21) Appl. No.: 12/799,609

(22) Filed: Apr. 28, 2010

(65) Prior Publication Data

US 2011/0218637 A1 Sep. 8, 2011

Related U.S. Application Data

(60) Provisional application No. 61/339,680, filed on Mar. 8, 2010.

(51) Int. Cl.
*A61F 2/32* (2006.01)
(52) U.S. Cl. .................................................. 623/22.15
(58) Field of Classification Search .... 623/19.11–19.14, 623/22.11–22.15, 22.4–22.46, 23.11–23.14, 623/23.39–23.43
See application file for complete search history.

(56) References Cited

U.S. PATENT DOCUMENTS

| | | |
|---|---|---|
| 3,506,982 A | 4/1970 | Steffee |
| 3,837,008 A | 9/1974 | Bahler et al. |
| 3,868,730 A | 3/1975 | Kaufer et al. |
| 3,916,451 A | 11/1975 | Buechel et al. |
| 3,978,528 A | 9/1976 | Crep |
| 4,030,143 A | 6/1977 | Elloy et al. |
| 4,206,517 A | 6/1980 | Pappas et al. |
| 4,693,723 A | 9/1987 | Gabard |
| 4,792,337 A | 12/1988 | Müller |
| 4,846,840 A | 7/1989 | Leclercq et al. |
| 5,092,898 A | 3/1992 | Bekki et al. |
| 5,462,563 A * | 10/1995 | Shearer et al. ............. 623/20.11 |
| 6,010,535 A | 1/2000 | Shah |

(Continued)

FOREIGN PATENT DOCUMENTS

EP 0 322 493 B1 8/1991

(Continued)

OTHER PUBLICATIONS

Chen, Cheng-Fong; Chen, Wei-Ming; Yang, Chan-Tsung; Huang,Ching-Kuei; Chen, Tain-Hsiung; Hybrid Assembly of Metal Head and Femoral Stem From Manufacturers During Isolated Acetabular Revision;Artificial Organs, vol. 34, Issue 8, pp. E242-E245; Publ. Aug. 2010.

(Continued)

*Primary Examiner* — William H. Matthews
*Assistant Examiner* — Marcia Hoffman
(74) *Attorney, Agent, or Firm* — Norris, McLaughlin & Marcus, PA

(57) ABSTRACT

An interlocking reversed hip prosthesis including an acetabular cup being implanted in the acetabular cavity having an acetabular articular ball, firmly attached to the central portion of the cup via Morse taper. The femoral component having a hemispherical cup attached to the neck of the implant via Morse taper in a modular fashion thereby allowing use of several length necks. After implantation of the acetabular cup and the femoral cup, the two members are assembled together for relative movement. The acetabular cup secured by several screws or resorbable fixation studs. During range of motion, the edge of the femoral cup becomes inserted into space located between the acetabular cup and the acetabular ball and becomes restrained thus reducing the likelihood of dislocation during extreme range of motion.

17 Claims, 4 Drawing Sheets

U.S. PATENT DOCUMENTS

| | | |
|---|---|---|
| 6,790,234 B1 | 9/2004 | Frankle |
| 6,800,095 B1 | 10/2004 | Pope et al. |
| 7,011,686 B2 | 3/2006 | Ball et al. |
| 7,033,396 B2 | 4/2006 | Tornier |
| 7,169,184 B2 | 1/2007 | Pria |
| 7,175,663 B1 | 2/2007 | Stone |
| 7,241,314 B1 | 7/2007 | Winslow |
| 7,309,360 B2 | 12/2007 | Tornier et al. |
| 7,462,197 B2 | 12/2008 | Tornier et al. |
| 7,465,319 B2 | 12/2008 | Tornier |
| 7,470,287 B2 | 12/2008 | Tornier |
| 7,611,539 B2 | 11/2009 | Bouttens et al. |
| 7,854,768 B2 | 12/2010 | Wiley et al. |
| 2002/0143402 A1 | 10/2002 | Steinberg |
| 2002/0173853 A1 | 11/2002 | Corl, III et al. |
| 2003/0114934 A1 | 6/2003 | Steinberg |
| 2003/0120347 A1 | 6/2003 | Steinberg |
| 2004/0039449 A1 | 2/2004 | Tornier |
| 2004/0220673 A1 | 11/2004 | Pria |
| 2005/0165490 A1 | 7/2005 | Tornier |
| 2005/0288791 A1 | 12/2005 | Tornier et al. |
| 2006/0069443 A1* | 3/2006 | Deffenbaugh et al. .... 623/19.11 |
| 2009/0113238 A1 | 4/2009 | Liu et al. |
| 2009/0192621 A1 | 7/2009 | Winslow |
| 2009/0287309 A1 | 11/2009 | Walch et al. |
| 2010/0131073 A1 | 5/2010 | Meridew et al. |
| 2010/0222886 A1 | 9/2010 | Wiley et al. |
| 2011/0054628 A1 | 3/2011 | Banks et al. |
| 2011/0151259 A1 | 6/2011 | Jarman-Smith et al. |
| 2011/0218637 A1 | 9/2011 | Termanini |
| 2011/0218638 A1 | 9/2011 | Termanini |
| 2011/0218645 A1 | 9/2011 | Garcia Saban et al. |
| 2011/0230590 A1 | 9/2011 | Jarman-Smith et al. |
| 2012/0116533 A1* | 5/2012 | Forsell ................ 623/23.11 |

FOREIGN PATENT DOCUMENTS

| | | |
|---|---|---|
| EP | 1 508 315 A2 | 2/2005 |
| EP | 1 543 801 B1 | 8/2007 |
| FR | 2603476 A1 | 3/1988 |
| FR | 2841768 A1 | 1/2004 |
| JP | 1175846 A | 7/1989 |
| JP | 200473854 A | 3/2004 |
| JP | 2005177496 A | 7/2005 |
| TW | 201112996 A | 4/2011 |
| WO | WO9710776 A3 | 3/1997 |
| WO | WO 2011/006852 A1 | 1/2011 |

OTHER PUBLICATIONS

Beldame, J.; Carreras, F.; Oger, P.; Beaufils, P.; Cementless cups do not increase osteolysis risk in metal-on-metal total hip arthroplasty; Orthopaedics & Traumatology-Surgery & Research, vol. 95, Issue 7, pp. 478-490, Publ. Nov. 2009, Elsevier Masson SAS.

Pavelka, T; Linhart, M; Houcek, P.; [Hip joint arthroplasty following surgical treatment of acetabular fracture]—Aloplastika kycelnihokloubu po operacnim leceni zlomenin acetabula; Acta chirurgiae orthopaedicae et traumatologiae Cechoslovaca, vol. 73, Issue 4, pp. 268-274; Publ. Aug. 2006.

Hamadouche, M; Madi, F.; Kerboull, L.; Courpied, Jr.; Kerboull, M.; Early femoral osteolysis following Charnley-Kerboull total hip arthroplsty combining a 22-mm zirconia head on polyethylene; Revue De Chirurgie Orthopedique et Reparatrice De L Appareil Moteur, vol. 91, Issue 5, pp. 439-445, Publ. Sep. 2005, Elsevier SAS.

Bal, BS; Vandelune, D.; Gurba, DM; Jasty, M.; Harris, WH; Polyethylene wear in cases using femoral stems of similar geometry, but different metals, porous layer, and modularity; Journal of Arthroplasty, vol. 13, Issue 5, pp. 492-499; Publ. Aug. 1998.

Schreurs, B. Willem; Van Tienen, Tony G.; Buma, Pieter; Verddonschot, Nico; Gardeniers, Jean WM; Slooff, Tom JJH; Favorable results of acetabular reconstruction with imkpacted morsellized bone grafts in patients younger than 50 years: A 10- to 18-year follow-up study of 34 cemented total hip arthroplasties;Journal: Acta orthopaedica Scandinavica,72 (2), 120-126; Publ. 2001, INIST-CNRS.

A. Roth, K. Sander, F. Layher, J. Babisch, R. Venbrocks; "In vivo measurement of polyethylene wear in cementless total hip arthroplasty"; Acta Chir Orthop Traumatol Cech. Feb. 2010;77(1):13-7; Clinic of Orthopaedics, Rudolf-Elle Hospital, Department of Orthopoaedies of the Friedrich-Schiller University of Jena, Eisenberg, Germany; ajroth@gmx.de.

G. Schmidig, A. Patel, I. Kiepins, M, Thakore, DC Markel; "The effects of acetabular shell deformation and liner thickness on frictional torque in ultrahigh-molecular-weight polyethylene acetabular bearings"; J. Arthroplasty, Jun. 2010; 25(4):644-53, Epub Jun. 2, 2009; Stryker Orthopaedics, Mahway, New Jersey, USA.

H. Ito, A. Minami T. Matsuno, H. Tanino, T. Yuhta, I. Nishimura; "The sphericity of the bearing surface in total hip arthroplasty"; J. Arthroplasty, Dec. 2001;16(18):1024-9; Department of Orthopaedic Surgery, Hokkaido University, School of Medicine, Sapporo, Japan; itobiro@med.hokudai.ac.jp.

P. Hernigou, T. Bahrami; "Zirconia and alumina ceramics in comparison with stainless-steel heads. Polyethylene wear after a minimum ten-year follow-up"; J Bone Joint Surg. Br. May 2003;85(4):504-9.

D. Dowson, ZM Jin; Metal-on-metal hip joint tribology; Proc Inst Mech Eng H. Feb. 2006;220(2):107-18.

International Search Reportdated May 9, 2011 from US International Searching Authority.

* cited by examiner

INTERLOCKING REVERSE HIP PROSTHESIS AND METHOD

CROSS REFERENCE TO RELATED APPLICATION

This application claims the benefit of U.S. Provisional Patent Application Ser. No. 61/339,680 filed on Mar. 8, 2010 and entitled "INTERLOCKING REVERSE HIP PROSTHESIS," the entirety of which is incorporated herein by reference.

BACKGROUND OF THE INVENTION

1. Field of the Invention

The present invention relates generally to hip prostheses and more specifically to an interlocking reverse hip prosthesis allowing increased range of motion and stability during excessive ranges of motion.

2. Description of the Prior Art

It can be appreciated that several hip implants have been in use for years. Typically, a conventional hip implant comprises a femoral component having an articulating femoral ball attached to a stem, which is inserted into the medullary canal of the femur after preparation and reaming using appropriate reamers by the operating surgeon. Said stem can be secured with bone cement or press fit. An acetabular component or socket having the shape of a cup is inserted into the acetabular cavity after preparation and appropriate reaming and secured with cancellous screws through holes in the implant, bone cement or press fit or a combination thereof.

The acetabular cup will then receive a lining made of high-density polyethylene or ceramic. Said lining will be secured into the acetabular cup by a press fit mechanism. The main problem with conventional hip implants is the instability of the prosthesis at the extreme ranges of motion thereby allowing the femoral ball to dislodge and dislocate. Prior art teaches constrained and preassembled ball and socket devices or a device wherein the ball and socket members are implanted separately whereupon the ball element is forced into a resilient opening in the socket and thereafter held in place by the resilient material. Other constrained acetabular sockets include a locking ring such as the one described by Albertorio et al. U.S. Pat. No. 6,527,808. In the case of socket elements having a retaining ring, the ball member is forcefully inserted into the socket after the two elements are implanted. This constitutes a weak link where forces exerted on the prosthesis by ambulatory motion may exceed the forces used to assemble the implant thereby causing the ball to be separated from the socket.

While these devices may be suitable for the particular purpose to which they address, they are not suitable for providing an interlocking mechanism as in the reverse hip implant design of the present invention, which by the very nature of its design allows increased range of motion and increased stability at extreme ranges of motion thereby reducing the risk of dislocation.

In these respects, the interlocking reverse hip prosthesis according to the present invention substantially departs from the conventional concept and design of the prior art, and in so doing provides an apparatus primarily developed for the purpose of reducing the risk of dislocation of hip implants at extreme ranges of motion. Furthermore, since the articulating surfaces of the two components are fully in contact 100% of the time, it is clear that this will improve the weight distribution and decrease the wear of the surfaces in contact and reduce the number of wear particles released in the joint. The later, being very detrimental to the proper function of the joint.

BRIEF DESCRIPTION OF THE DRAWINGS

Various other objects, features and advantages of the present invention will become fully appreciated as the same becomes better understood when considered in conjunction with the current accompanying drawings, in which like reference characters designate the same or similar elements throughout the several views, and wherein.

SUMMARY OF THE INVENTION

Figure 1:
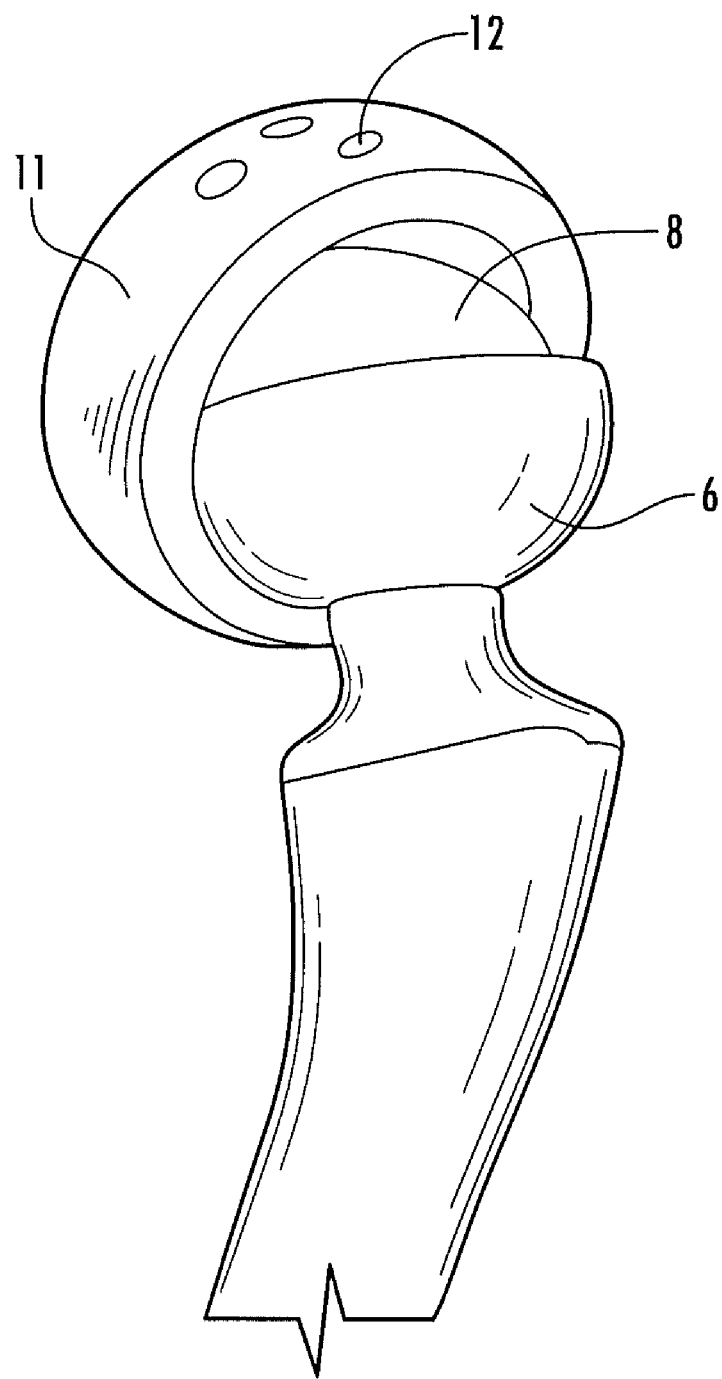
FIG. 1 is a perspective view of the interlocking reverse hip prosthesis.
Figure 2:
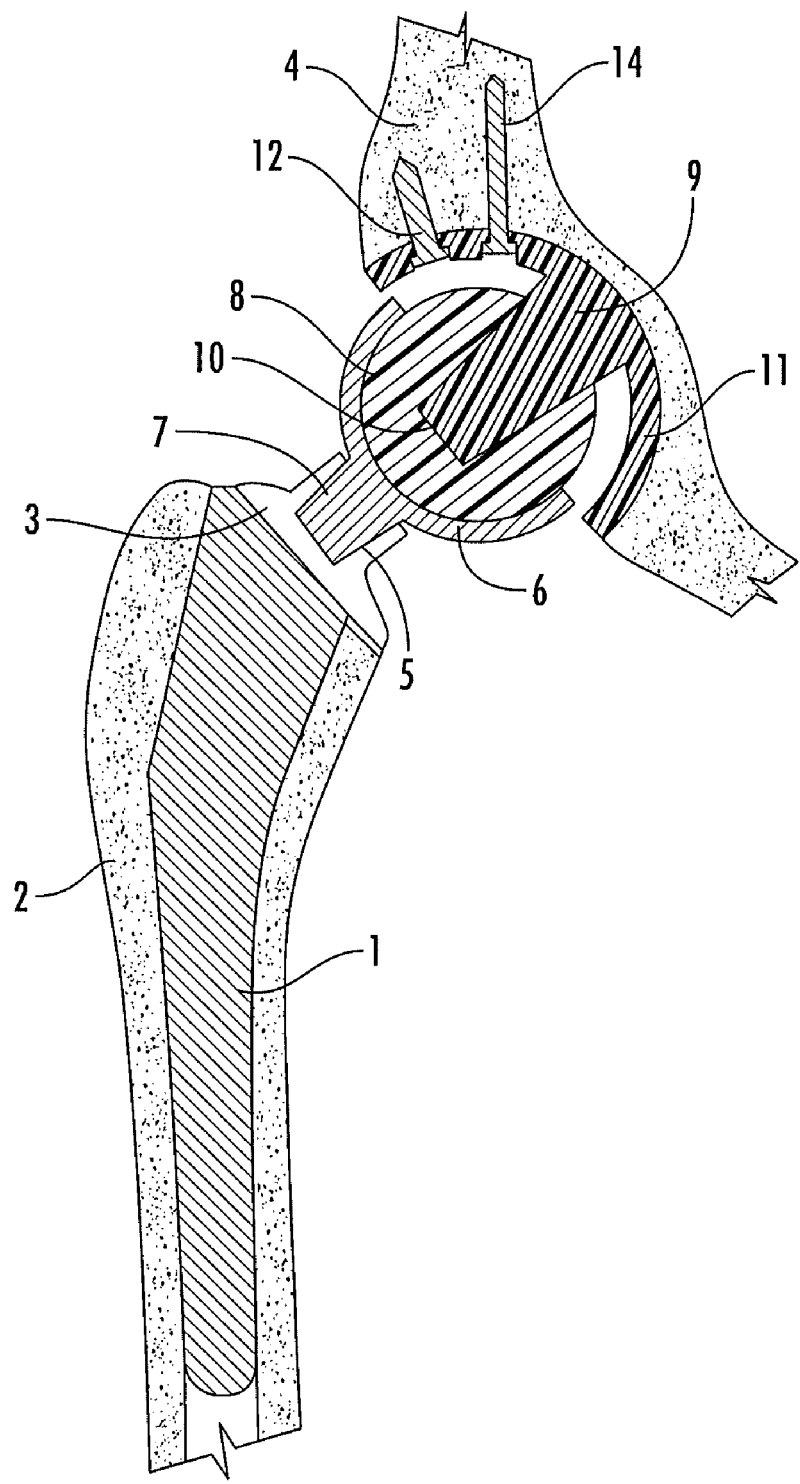
FIG. 2 is a sectional view of the interlocking reverse hip prosthesis.
Figure 3:
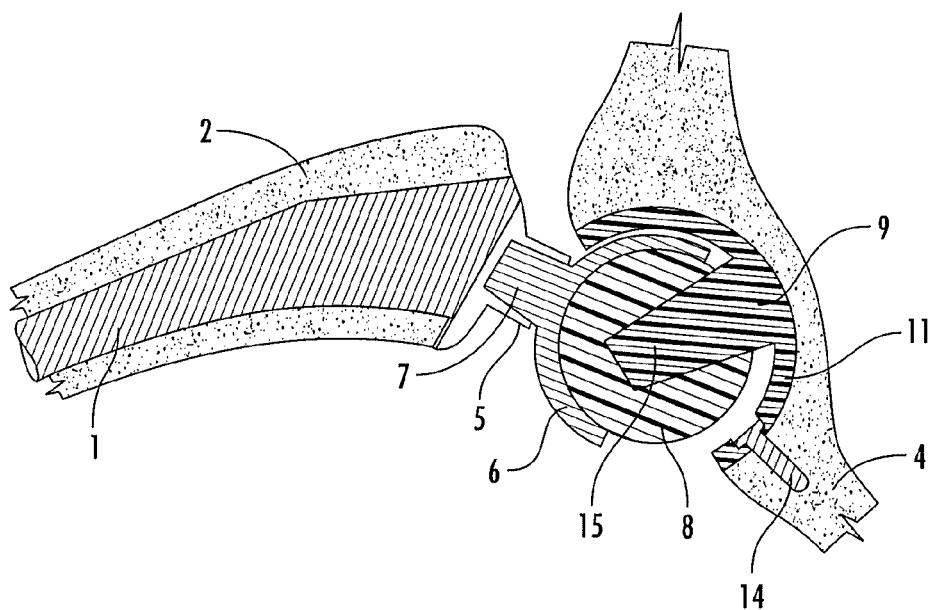
FIG. 3 is a sectional view of the interlocking reverse hip prosthesis in extension and external rotation.
Figure 4:
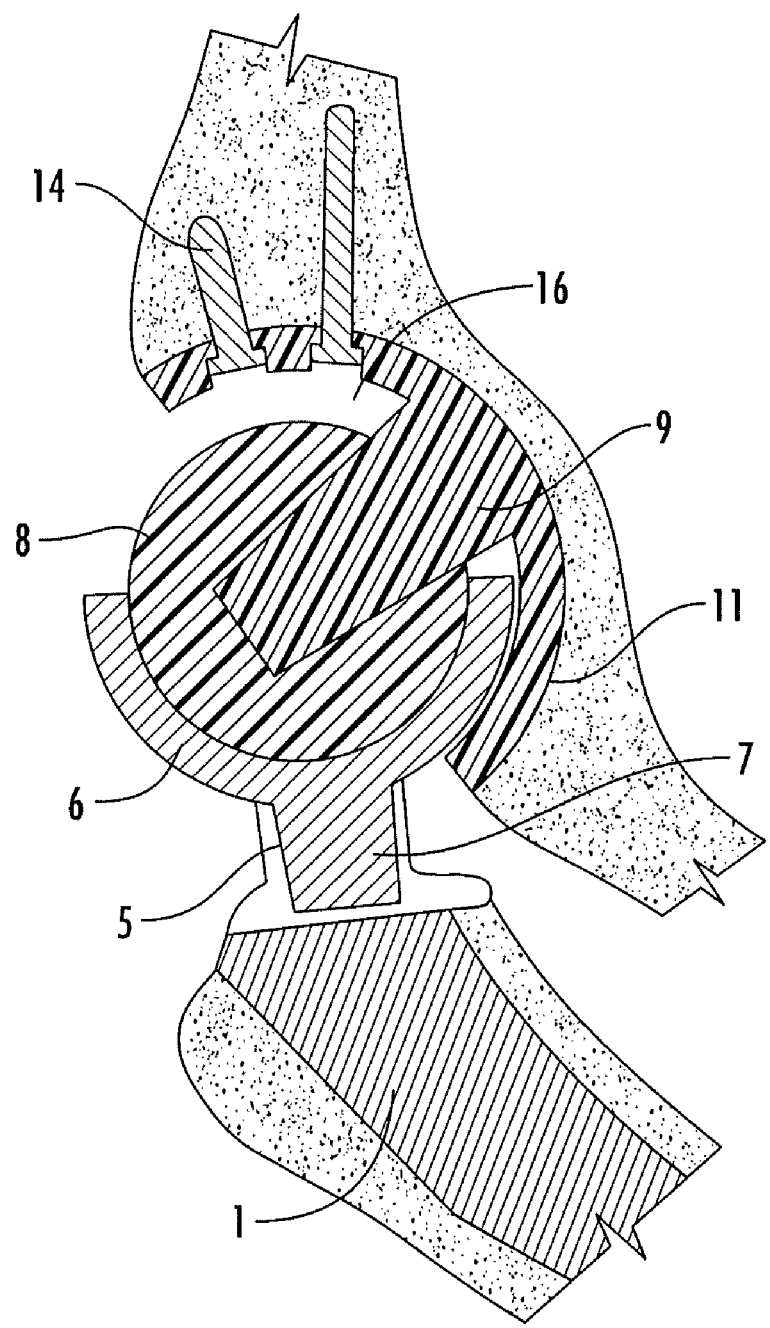
FIG. 4 is a sectional view of the interlocking reverse hip prosthesis in flexion and internal rotation.

The present invention provides a new interlocking reverse hip prosthesis construction wherein an articulating acetabular ball member of the acetabular component is solidly and concentrically attached to the a central protrusion or stem of an acetabular cup via Morse taper. A hemispherical femoral cup member is solidly attached to a femoral stem via Morse taper. Said acetabular cup or socket is implanted in an acetabular opening or cavity constructed by the surgeon into the pelvic bone to which it is firmly secured by one or more screws through one or more openings in the acetabular cup. In another embodiment of this invention the screws can be replaced by biocompatible resorbable studs of variable number. The femoral stem is then inserted and impacted into the femoral medullary canal which has been prepared and hollowed by the surgeon using appropriate reamers. The femoral hemispherical articulating cup is then firmly attached to the proximal end of the femoral stem via Morse Taper. Subsequently, the hip is reduced and the femoral and acetabular components are put in contact whereby the femoral hemispherical cup will concentrically glide over the articulating acetabular ball. During ambulation, the femoral cup edge or lip will glide conformably into a hemispherical space (16) located between the acetabular articular ball and the acetabular cup. Furthermore, by its very geometrical configuration, it becomes very difficult for the femoral cup to dislocate when the range of motion increases since it becomes constrained in the hemispherical locking space between the acetabular cup and the acetabular ball.

Furthermore, since the articulating surfaces of the two components are fully in contact 100% of the time, it is clear that this will improve the weight distribution and decrease the wear of the surfaces in contact and reduce the number of wear particles released in the joint.

There has thus been outlined, rather broadly, the more important features of the invention in order that the detailed description may be better understood, and in order that the present contribution to the art may be better appreciated. The novel feature of this invention, whereby the location of the articulating surfaces of the hip joint, namely the ball and socket, is reversed, resulting in a new restrained reverse hip prosthesis which is not anticipated, rendered obvious, suggested or even implied by any prior conventional hip prosthesis, either alone or in any combination thereof.

In this respect, before explaining at least one embodiment of the invention in detail, it is to be understood that the invention is not committed in its application to the details of construction and the arrangements of the component set forth in the following description or illustrated in the drawings. The invention is capable of other embodiments and of being practiced and carried out in various ways. Also, it is to be understood that the terminology employed herein is for the purpose of the description and should not be regarded as limiting.

To the accomplishment of the above and related objects, this invention may be embodied in the form illustrated in the accompanying drawings. Attention being called to the fact, however, that the drawings are elicited only, and that changes may be made to any specific construction illustrated.

DETAILED DESCRIPTION OF THE ENABLING EMBODIMENTS

Turning now descriptively to the drawings, in which similar reference characters denote similar elements throughout the several views, the attached figures illustrate an interlocking reverse hip prosthesis, which comprises a hemispherical acetabular cup (11) having a smooth concave surface and a convex non-articulating surface. The convex non-articulating surface provides a porous surface with multiple asperities and micro-voids to allow bone ingrowth. Furthermore, the acetabular cup (11) provides one or more holes (12) at different locations for the purpose of using one or more screws (14). In another embodiment, the screws (14) can be replaced with resorbable nonmetallic and biocompatible studs of different diameter and length. These orthobiologic resorbable studs will secure the acetabular cup (11) shell during the initial phase of bone ingrowth and will resorb within one year, being replaced by newly generated bone and become part of the host bone. During that period, the acetabular cup (11) is by then solidly attached to the acetabular bone by bone ingrowth. The concave hemispherical surface of the acetabular cup (11) provides a large interior cylindrical protrusion or stem (9), which has a male Morse taper (15) for assembly to the female Morse taper (10) of the acetabular ball (8). The hemispherical articulating femoral cup (6) has a central cylindrical protrusion (7) on its convex surface, which has a male Morse taper for assembly to a recess (5) with a female Morse taper located at the shoulder (3) of the femoral stem (1). The central protrusion (7) of the femoral cup (6) comes in different lengths thereby allowing use of several neck lengths in a modular fashion.

In another embodiment of the invention, the articulating femoral cup (6) will have a female Morse taper while the femoral stem (1) would have a male Morse taper.

An important advantage of the present invention is that the greater the interdigitation the more stability of the implant as opposed to the conventional femoral ball and socket hip implants, where increased range of motion is usually associated with increased risk of dislocation.

During the implementation of the prosthesis of the present invention, the operating surgeon will initially prepare the proximal femoral bone (2) by using conventional reamers in the usual fashion. The acetabular cavity in the pelvic bone (4) is reamed to the appropriate size to accept the acetabular cup (11), which is impacted for press fit at the right angle of inclination and orientation. Fixation screws or biocompatible resorbable studs are then inserted in place to secure the acetabular cup (11). The femoral stem (1) is then inserted into the femoral canal and can be cemented or press fit. The acetabular ball (8) is then inserted onto the central protrusion or stem (9) of the acetabular cup (11). Subsequently, the articulating femoral cup (6) is inserted onto the proximal femoral stem via Morse taper (5). Once the insertion of the components is complete, the implant is assembled together.

In one embodiment, the articulating surface of the femoral cup (6) contains a high molecular weight polyethylene lining of varying thickness, but no less than 4 mm. In a different embodiment the lining could be porcelain or other metallic alloy.

Another embodiment is directed to prosthesis for a shoulder joint. The first component includes an anchoring glenoid plate attached to the concave surface of the glenoid fossa having a glenoid ball. The second component being a hemispherical humeral cup having a stem like protrusion, which is attached via Morse taper to a humeral stem to be inserted into the proximal humerus.

It is therefore the object of the present invention to provide a new and improved interlocking and restrained reverse hip prosthesis system, where the conventional articulating surfaces of the hip joint are reversed and interlocked. The system described in the present invention, has all the advantages of the prior art of known design and configuration and none of the disadvantages.

With respect to the above description then, it is to be realized that the optimum dimensional relationships for the parts of the invention, to include variations in size, material, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A reverse hip prosthesis comprising a unitary acetabular cup having a convex non-articulating surface for attachment to an acetabular socket in a pelvic bone and a concave surface located opposite to the convex non-articulating surface, the concave surface having an acetabular cup stem firmly affixed therein and projecting outwardly therefrom, an acetabular ball firmly affixed to the acetabular cup stem, the acetabular ball having a surface, the concave surface of the acetabular cup and the surface of the acetabular ball are spaced from one another, thereby defining a gap therebetween, a femoral implant for implantation in a medullary canal of a proximal end of a femur, and a femoral cup firmly affixed to a proximal end of the femoral implant, the femoral cup sized for articulation in the gap, such that the femoral cup has a concave surface sized for articulation on the surface of the acetabular ball and a convex surface opposite the concave surface of the femoral cup sized for articulation on the concave surface of the acetabular cup, the gap being sized and configured to permit said articulations while constraining the femoral cup within the gap throughout an entire range of said articulations of the femoral cup as it articulates within the gap, thereby reducing the risk of dislocation.

2. The prosthesis of claim 1 wherein the concave surface of the acetabular cup is hemispherical, the acetabular ball is spherical and the concave surface of the femoral cup is hemispherical.

3. The prosthesis of claim 1 wherein the concave surface of the acetabular cup has a center and the acetabular cup stem is affixed to and in the center.

4. The prosthesis of claim 1 wherein the acetabular ball has an acetabular ball recess sized to receive the acetabular cup stem.

5. The prosthesis of claim 4 wherein the acetabular ball has a center, the acetabular cup stem has a longitudinal center line and the acetabular ball recess has a longitudinal center line, both longitudinal center lines being colinear and passing through the center of the acetabular ball.

6. The prosthesis of claim 1 wherein the femoral cup has a femoral cup stem projecting outwardly therefrom in a direction opposite the concave surface thereof and the femoral implant has at its proximal end a recess sized to receive the femoral cup stem.

7. The prosthesis of claim 6 wherein the concave surface of the femoral cup is hemispherical and has a center line, the femoral cup stem has a longitudinal center line and the femoral implant recess has a longitudinal center line wherein all of the center lines are colinear.

8. A reverse hip prosthesis comprising
a unitary acetabular cup having an outer non-articulating surface adapted for attachment to an acetabular socket in a pelvic bone and a concave surface located opposite to the non-articulating surface, the concave surface having an acetabular cup stem firmly affixed therein and projecting outwardly therefrom,
an acetabular ball firmly affixed to the acetabular stem, the acetabular ball having a surface,
the concave surface of the acetabular cup and the surface of the acetabular ball are spaced from one another, thereby defining a gap therebetween,
a femoral implant for implantation in a medullary canal of a proximal end of a femur, and
a femoral cup firmly affixed to a proximal end of the femoral implant, the femoral cup sized for articulation in the gap, such that the femoral cup has a concave surface sized for articulation on the surface of the acetabular ball and a convex surface opposite the concave surface of the femoral cup sized for articulation on the concave surface of the acetabular cup, the gap being sized and configured to permit said articulations while constraining the femoral cup within the gap throughout an entire range of said articulations of the femoral cup as it articulates within the gap, thereby reducing the risk of dislocation.

9. The prosthesis of claim 8 wherein the concave surface of the acetabular cup is hemispherical, the acetabular ball is spherical and the concave surface of the femoral cup is hemispherical.

10. The prosthesis of claim 8 wherein the concave surface of the acetabular cup has a center and the acetabular cup stem is affixed to and in the center.

11. The prosthesis of claim 8 wherein the acetabular ball has an acetabular ball recess sized to receive the acetabular cup stem.

12. The prosthesis of claim 11 wherein the acetabular ball has a center, the acetabular cup stem has a longitudinal center line and the acetabular ball recess has a longitudinal center line, both longitudinal center lines being colinear and passing through the center of the acetabular ball.

13. The prosthesis of claim 8 wherein the femoral cup has a femoral cup stem projecting outwardly therefrom in a direction opposite the concave surface thereof and the femoral implant has at its proximal end a recess sized to receive the femoral cup stem.

14. The prosthesis of claim 13 wherein the concave surface of the femoral cup is hemispherical and has a center line, the femoral cup stem has a longitudinal center line and the femoral implant recess has a longitudinal center line wherein all of the center lines are colinear.

15. The prosthesis of claim 8 wherein the concave surface of the femoral cup is fully in contact with the surface of the acetabular ball during articulation of said concave surface of the femoral cup on the acetabular ball.

16. The prosthesis of claim 8 wherein the gap is hemispherical.

17. A method of implanting in a patient the prosthesis of claim 8 comprising preparing an acetabular socket in a pelvis and affixing the acetabular cup therein, preparing a medullary canal at the proximal end of a femur and affixing the femoral implant therein, affixing the acetabular ball to the acetabular cup stem, affixing the femoral cup to the proximal end of the femoral implant and aligning the concave surface of the femoral cup with the acetabular ball so that the femoral cup will articulate in the gap and the concave surface of the femoral cup will articulate on the surface of the acetabular ball.

* * * * *